United States Patent

Schweizer et al.

[11] Patent Number: 6,055,047
[45] Date of Patent: Apr. 25, 2000

[54] DEVICE FOR DETERMINING THE DEGREE OF WEAR OF A PAPER TRANSPORT ROLLER

[75] Inventors: Andreas Schweizer, Bad Ditzenbach; Reinhard Weltz, Leonberg, both of Germany

[73] Assignee: Eastman Kodak Company, Rochester, N.Y.

[21] Appl. No.: 09/081,986

[22] Filed: May 20, 1998

[30] Foreign Application Priority Data

May 30, 1997 [DE] Germany .................... 197 22 593

[51] Int. Cl.[7] .................... G01N 21/88; G01N 21/47
[52] U.S. Cl. .................... 356/237.1; 356/446
[58] Field of Search .................... 356/237.1, 446; 271/265.01, 258.01, 314; 198/10.03, 502.1; 492/53

[56] References Cited

U.S. PATENT DOCUMENTS

| | | | |
|---|---|---|---|
| 4,763,637 | 8/1988 | Mayer | 125/21 |
| 5,199,703 | 4/1993 | Hess | 271/314 |
| 5,379,994 | 1/1995 | Kushida | 271/265.01 |
| 5,394,227 | 2/1995 | Huffman et al. | |
| 5,435,543 | 7/1995 | Lehmann | |
| 5,553,845 | 9/1996 | Sawa et al. | 271/314 |

FOREIGN PATENT DOCUMENTS

| | | |
|---|---|---|
| 0 146 917 B1 | 3/1990 | European Pat. Off. |
| 0 653 688 A1 | 5/1995 | European Pat. Off. |
| 93 00 919 | 5/1993 | Germany . |
| 6-227784 | 2/1993 | Japan . |
| 1594488 | 7/1981 | United Kingdom .................... 217/317 |

Primary Examiner—Frank G. Font
Assistant Examiner—Zandra V. Smith
Attorney, Agent, or Firm—Francis H. Boos, Jr.

[57] ABSTRACT

The degree of wear of the paper transport roller (10) is checked by means of a reflected light barrier (40). To that end, the paper transport roller (10) comprises two layers (13 and 15) applied to the core of the paper transport roller (10). The two layers (13 and 15) differ in their degree of reflection for electromagnetic radiation. The layers (13 and 15) are applied to the paper transport roller (10) such that the inner layer (13) has a lower degree of reflection than the outer layer (15). The inner layer (13) is advantageously black and the outer layer (15) white. When the outer layer (15) is worn as a result of the friction between the single sheet (30) to be transported and the paper transport roller (10), the inner layer (13) gradually comes into contact with the single sheets. The degree of reflection of the surface of the paper transport roller (10) then also changes in the same way and is determined using a reflected light barrier (40). The user is therefore signaled that the paper transport roller (10) must be replaced.

14 Claims, 1 Drawing Sheet

DEVICE FOR DETERMINING THE DEGREE OF WEAR OF A PAPER TRANSPORT ROLLER

FIELD OF THE INVENTION

The invention relates to a device for determining the degree of wear of a paper transport roller, said device comprising at least two materials differing in their degree of reflection for electromagnetic radiation, and one reflected light barrier arranged above the paper transport roller with a downstream-connected electronic unit for determining the amount of electromagnetic radiation reflected from the surface of the paper transport roller.

BACKGROUND OF THE INVENTION

The German utility model DE-GM-93 00 919 describes a movement control device for moving objects. A ball rests on the moving object and is driven by the linear movement of the object. Material embedments are provided on the circumference of the ball and generate, together with a signal device, the movement signals to be determined. In accordance with a modification of the invention, the material embedments have optical properties differing from the remaining surface of the ball and picked up by a reflected light barrier aligned with the surface of the ball.

EP-B-0 146 917 discloses a system for recognition of the presence of a transported article on the casing surface of a rotating transport element. Inside the casing of the transport element, two openings are provided for receiving the ends of an optical waveguide. The optical waveguides pass the optical information to a stationary component in which a light transmitter and a light receiver are accommodated. An evaluation circuit converts the signals into a control signal indicating the presence or absence of a transported article. It is here immediately clear to a person skilled in the art that the scanning of the surface of the rotating transport element from the inside is mechanically difficult and hence unnecessarily increases the cost of a transport element.

EP-A-0 653 688 shows that it is known for a roll (in this case a contact pressure roller against a fuser roller) to comprise at least two layers of differing materials. The roller comprises a deformable material and a harder outer shell or casing.

SUMMARY OF THE INVENTION

It is the object of the present invention to create a device that determines the wear or the degree of wear of a paper transport roller regardless of the number of copies processed.

A further object of the invention is to indicate to the user in good time that a certain component has to be replaced on account of wear, in order to prevent a failure of the end processing unit due to failure of the paper alignment function.

This object is attained in accordance with the invention in that the materials with the differing degree of reflection are applied in layers to the paper transport roller such that an outer layer has a higher degree of reflection than an inner layer.

The advantage of the device is that the failure of, for example, an end processing unit on account of failure of the paper alignment function is ruled out, since it is indicated to the user when the paper transport roller has attained a certain degree of wear and needs replacement. This avoids the need to replace the paper transport roller at regular intervals, as required for conventional devices. In addition, variances of the friction coefficients of the paper grades used can be checked, which in the final analysis increases the dependability of paper transport or paper alignment. The degree of wear of the paper transport roller is checked using a reflected light barrier. To that end, the paper transport roller comprises two layers applied to the core of the paper transport roller. These two layers differ in their degree of reflection for electromagnetic radiation. The layers are applied to the paper transport roller such that the inner layer has a lower degree of reflection than the outer one. The inner layer is advantageously black and the outer layer white. When the outer layer is worn as a result of the friction between the single sheet to be transported and the paper transport roller, the inner layer gradually comes into contact with the single sheets. The degree of reflection of the surface of the paper transport roller then also changes in the same way and is ascertained using a reflected light barrier. The user is therefore signaled that the paper transport roller must be replaced.

Further advantageous modifications of the invention can be inferred from the sub-claims.

BRIEF DESCRIPTION OF THE DRAWINGS

The subject matter of the invention will be described with reference to the embodiment shown in the drawing in which.

DETAILED DESCRIPTION OF THE INVENTION

Figure 1:
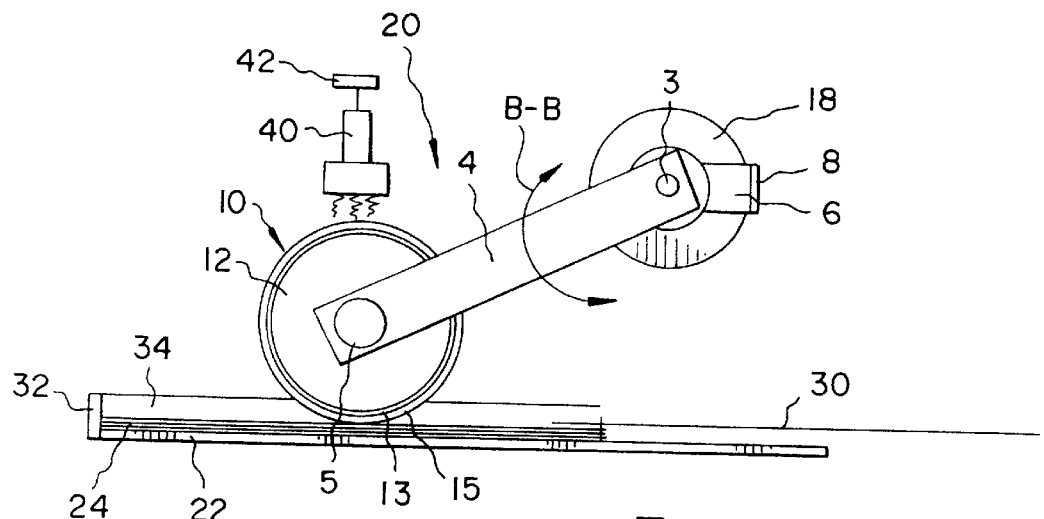
FIG. 1 shows a diagrammatic side view of the device and FIG. 2 shows a plan view, where the incoming paper sheets are to be aligned on two lay edges.
Figure 2:
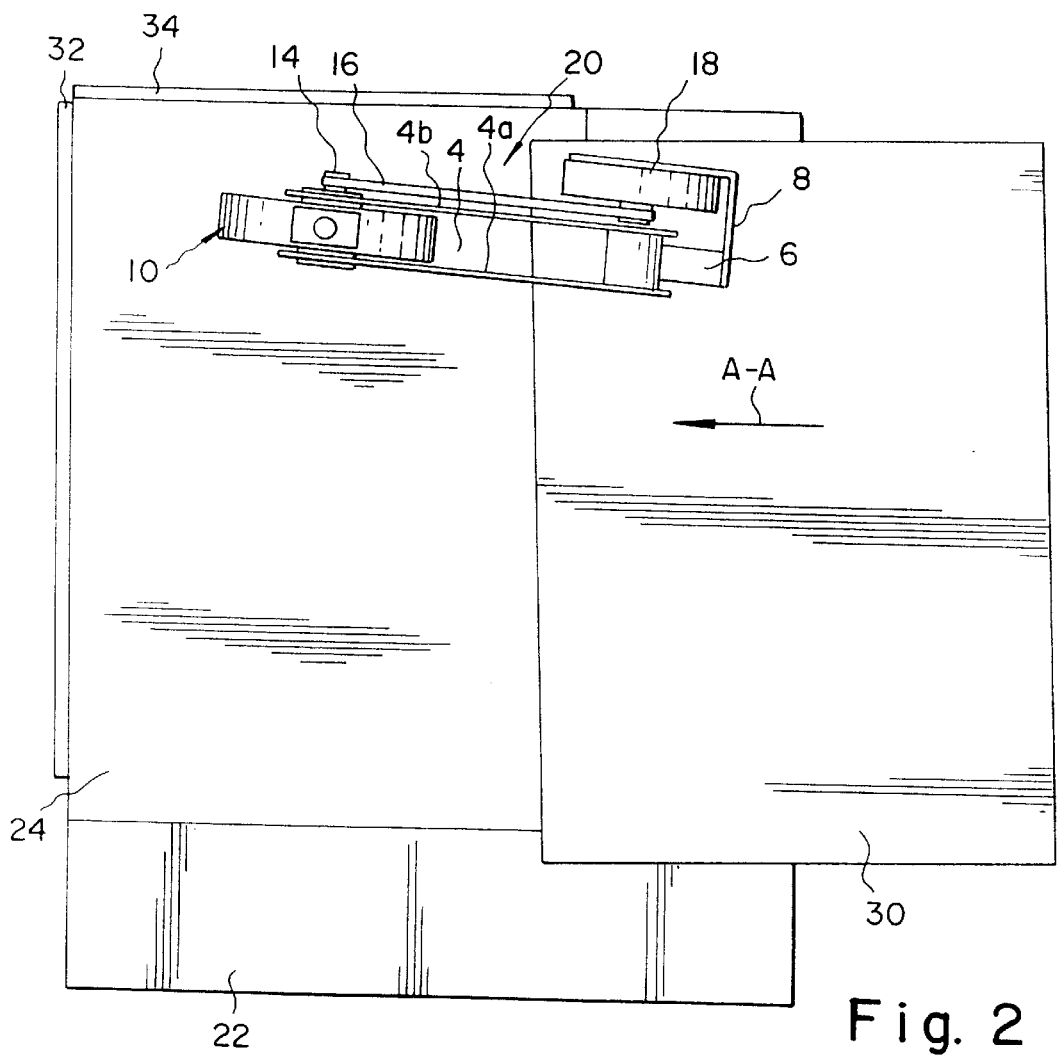

An embodiment of the invention is shown in FIGS. 1 and 2. Here a paper transport roller 10 is installed in a jogging device 20 by which a single sheet 30 can be aligned in relation to a first and second lay edge 32 and 34 respectively. The two lay edges 32 and 34 are arranged vertically to one another.

It is obvious for a person skilled in the art that the device for determining the degree of wear of a paper transport roller is not restricted exclusively to jogging devices; the device can be used wherever a friction force prevails between the paper to be transported and the paper transport roller and in the final analysis leads to friction wear of the latter. The further description confines itself exclusively to a paper transport roller 10 which forms part of the jogging device 20.

In a final processing unit for paper sheets, single sheets 30 are collected on a support surface 22 to form a sheet stack 24, with each single sheet 30 on the sheet stack 24 being aligned with the first and second lay edges 32 and 34 perpendicular to one another. To achieve the alignment, the paper transport roller 10 is arranged above the sheet stack 24 or the support surface 22 such that the paper transport roller 10 permanently rests on the accumulating sheet stack 24 and at the same time compensates for the thickness of the growing sheet stack 24. If a single sheet 30 is supplied to the sheet stack 24, it is picked up by the paper transport roller 10, which is at an angle to the transport direction A—A of the incoming single sheet 30. The reason for the inclination of the paper transport roller 10 against the first and second lay edges 32 and 34 is that as a result the single sheet 30 is movable towards the lay edges 32 and 34 perpendicular to one another.

If the single sheet is in contact with one of the lay edges 32 or 34, it cannot perform a forward movement in the direction of the respective lay edge 32 or 34. Since the paper transport roller 10 continues nevertheless to rotate, friction wear results on the circumference of the paper transport roller 10 until the next single sheet is supplied to the sheet stack 24.

As already mentioned above, the jogging device 20 is arranged above the support surface 22 or sheet stack 24. The jogging device 20 comprises a drive motor 18, whose rotary movement is transmissible via a belt 16 (also toothed belt or drive chain) to a hub 14 of the paper transport roller 10. The drive motor 18 is attached to a holder 8 that in turn is permanently connected to a housing part (not shown). A fastening element 6 is furthermore attached to the holder 8, to which element a holding element 4 for the paper transport roller 10 is swivelably connected. The holding element 4 performs the swivel movement shown by the arrow B—B in FIG. 1 vertical to the support surface 22, so that the jogging device 20 can adjust to the changing height of the sheet stack. To perform the swivel movement, a swivel axis 3 for the holding element 4 is provided in the fastening element. At that end of the holding element 4 opposite the swivel axis 3, a bearing 5 for the paper transport roller 10 is provided.

In the embodiment shown here, the holding element 4 comprises two holding rails 4a and 4b. The holding rails 4a and 4b are kept apart by the fastening element 6 and are parallel to one another. The clear distance between the holding rails 4a and 4b is dimensioned such that it is suitable for receiving, holding and supporting the paper transport roller 10.

The paper transport roller 10 for the jogging device 20 comprises a foam core 12 covered around its circumference by an inner layer 13 and an outer layer 15. The inner layer 13 is applied to the foam core. The outer layer 15 is applied to the inner layer 13 and is in contact with the single sheet 30 that is to be aligned. The materials of the inner and outer layers are selected such that there is a sufficient friction coefficient between the single sheet 30 to be aligned and the paper transport roller for alignment of the former, and such that a sufficient friction force is transferred between the single sheet 30 and the paper transport roller 10 to move the single sheet 30 forwards by means of the rotary movement of the paper transport roller. For example, the inner layer 13 and the outer layer 15 comprise a silicon material. In the embodiment, described here, the outer layer 15 is white and the inner layer 13 black.

Due to the friction between the single sheet 30 and the paper transport roller 10, the outer layer 15 of the paper transport roller 10 is subjected to wear. A reflected light barrier 40 is provided (fasteners not shown) such that the electromagnetic radiation (light) it emits falls directly on the circumference of the paper transport roller 10. The radiation is reflected from the white outer layer 15 to the reflected light barrier 40 and triggers a certain signal there. If the white outer layer 15 is almost completely worn away, the black inner layer 13 slowly appears until the white outer layer 15 has disappeared completely. In the transitional phase from the outer layer 15 to the inner layer 13, the color of the layer changes whereby the signal of the reflected light barrier 40 changes. This signal change is processed by an electronic unit 42 connected downstream of the reflected light barrier 40, and suitable software indicates to the user via a display (not shown) that the worn paper transport roller 10 must be replaced as soon as possible.

The invention has been described with reference to a preferred embodiment, however modifications can be made by those skilled in the art without leaving the scope of the claims below.

Parts List

3 Swivel axis
4 Holding element
4a Holding rail
4b Holding rail
5 Bearing
6 Fastening element
8 Holder for drive motor
10 Paper transport roller
12 Foam core
13 Inner layer
14 Hub
15 Outer layer
16 Belt
18 Drive motor
20 Jogging device
22 Support surface
24 Sheet stack
30 Single sheet
32 First lay edge
34 Second lay edge
40 Reflected light barrier
42 Electronic unit
A—A Transport direction of incoming single sheet
B—B Swivel direction of holding element

What is claimed is:

1. Roller wear determining device for determining the degree of wear of a paper transport roller (10), said device comprising at least two materials differing in their degree of reflection for electromagnetic radiation, and one reflected light barrier (40) arranged above said paper transport roller (10) with a downstream-connected electronic unit (42) for determining the amount of the electromagnetic radiation reflected from the surface of said paper transport roller (10), said materials with the differing degree of reflection being in layers on said paper transport roller (10) such that an outer layer (15) has a higher degree of reflection than an inner layer (13) characterized in that the paper transport roller (10) is usable for alignment of a single sheet (30) on at least one lay edge (32, 34) associated with a support surface (22).

2. Roller wear determining device according to claim 1, characterized in that the paper transport roller (10) permanently rests on an accumulating sheet stack (24) on said support surface (22) and at the same time has means for compensating for the thickness of the growing sheet stack (24).

3. Roller wear determining device for determining the degree of wear of a paper transport roller (10), said device comprising at least two materials differing in their degree of reflection for electromagnetic radiation, and one reflected light barrier (40) arranged above said paper transport roller (10) with a downstream-connected electronic unit (42) for determining the amount of the electromagnetic radiation reflected from the surface of said paper transport roller (10), said materials with the differing degree of reflection being in layers on said paper transport roller (10) such that an outer layer (15) has a higher degree of reflection than an inner layer (13) characterized in that the paper transport roller (10) is at an angle to the transport direction (A—A) of an incoming single sheet (30) on a sheet stack (24) on the support surface (22).

4. Roller wear determining device for determining the degree of wear of a paper transport roller (10), said device comprising at least two materials differing in their degree of reflection for electromagnetic radiation, and one reflected light barrier (40) arranged above said paper transport roller (10) with a downstream-connected electronic unit (42) for determining the amount of the electromagnetic radiation reflected from the surface of said paper transport roller (10), said materials with the differing degree of reflection being in layers on said paper transport roller (10) such that an outer layer (15) has a higher degree of reflection than an inner layer (13) characterized in that the paper transport roller (10) comprises a foam core (12) supporting said inner layer (13), which in turn supports said outer layer (15), and in that said inner layer (13) is black and said outer layer (15) is white.

5. Roller wear determining device according to claim 4, characterized in that said inner layer (13) and said outer layer (15) are silicon.

6. Roller wear determining device according to claim 4, characterized in that said outer layer can be worn as a result of the friction transmission between a single sheet (30) and said paper transport roller (10), in that the electromagnetic radiation of the reflected light barrier (40) falls on said inner layer (13) exposed by friction, in that light reflected from said inner layer (13) is discernible by said reflected light barrier (40) and recordable by the downstream-connected electronic unit (42), and in that a change in the discerned reflected light is displayable.

7. Roller wear determining device according to claim 6, characterized in that said display indicates that said paper transport roller (10) is to be changed.

8. Device for determining the degree of wear of a paper transport roller (10), said device comprising at least two materials differing in their degree of reflection for electromagnetic radiation, and one reflected light barrier (40) arranged relative to said paper transport roller (10) with a downstream-connected electronic unit (42) for determining the amount of the electromagnetic radiation reflected from the surface of said paper transport roller (10), said materials with the differing degree of reflection being in layers on said paper transport roller (10) such that an outer layer (15) has a higher degree of reflection than an inner layer (13), and said paper transport roller (10) being usable for alignment of a single sheet (30) on a first lay edge (32) and on a second lay edge (34), arranged at right angles thereto of a support surface (22).

9. Roller wear determining device according to claim 8, characterized in that said paper transport roller (10) permanently rests on an accumulating sheet stack (24) on said support surface (22) and at the same time has means for compensating for the thickness of the growing sheet stack (24).

10. Roller wear determining device according to claim 8, characterized in that said paper transport roller (10) is at an angle to the transport direction (A—A) of an incoming single sheet (30) on the sheet stack (24).

11. Roller wear determining device according to claim 10, characterized in that said paper transport roller (10) comprises a foam core (12) supporting said inner layer (13), which in turn supports said outer layer (15), and in that said inner layer, (13) is black and said outer layer (15) is white.

12. Roller wear determining device according to claim 11, characterized in that said inner layer (13) and said outer layer (15) are silicon.

13. Roller wear determining device according to claim 12, characterized in that said outer layer can be worn as a result of the friction transmission between a single sheet (30) and said paper transport roller (10), in that the electromagnetic radiation of the reflected light barrier (40) falls on said inner layer (13) exposed by friction, in that light reflected from said inner layer (13) is discernible by said reflected light barrier (40) and recordable by the downstream-connected electronic unit (42), and in that a change in the discerned reflected light is displayable.

14. Device according to claim 13, characterized in that said display indicates that said paper transport roller (10) is to be changed.

* * * * *